(12) United States Patent
Palero et al.

(10) Patent No.: US 11,229,805 B2
(45) Date of Patent: Jan. 25, 2022

(54) RADIO FREQUENCY SKIN TREATMENT DEVICE

(71) Applicant: KONINKLIJKE PHILIPS N.V., Eindhoven (NL)

(72) Inventors: Jonathan Alambra Palero, Eindhoven (NL); Martin Jurna, Eindhoven (NL); Margaret Ruth Horton, Eindhoven (NL); Babu Varghese, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 831 days.

(21) Appl. No.: 15/313,115

(22) PCT Filed: May 19, 2015

(86) PCT No.: PCT/EP2015/060938
§ 371 (c)(1),
(2) Date: Nov. 22, 2016

(87) PCT Pub. No.: WO2015/185352
PCT Pub. Date: Dec. 10, 2015

(65) Prior Publication Data
US 2017/0189704 A1   Jul. 6, 2017

(30) Foreign Application Priority Data

Jun. 4, 2014   (EP) .................................... 14171173

(51) Int. Cl.
*A61N 1/04* (2006.01)
*A61N 1/40* (2006.01)
(Continued)

(52) U.S. Cl.
CPC .......... *A61N 1/403* (2013.01); *A61N 1/0476* (2013.01); *A61N 1/0492* (2013.01); *A61N 1/06* (2013.01);
(Continued)

(58) Field of Classification Search
None
See application file for complete search history.

(56) References Cited

U.S. PATENT DOCUMENTS

2003/0225403 A1\* 12/2003 Woloszko ............ A61B 18/148
606/41
2006/0270942 A1   11/2006 McAdams
(Continued)

FOREIGN PATENT DOCUMENTS

KR       101065611 B1    9/2011
KR       101227224 B1    1/2013
(Continued)

*Primary Examiner* — Kaitlyn E Smith
*Assistant Examiner* — Yasamin Ekrami

(57) ABSTRACT

A device for skin treatment includes a non-circular symmetrical outer electrode and at least two inner electrodes surrounded by the outer electrode. An RF generator is arranged to supply an RF voltage between the inner electrodes and the outer electrode. If the outer electrode has two or more axes of symmetry, then each of the inner electrodes is at an equal minimum distance from the outer electrode and an equal distance from a common point of intersection of all axes of symmetry and is positioned, with respect to each of the respective axes of symmetry, either on the respective axis of symmetry or at a distance from the respective axis of symmetry and symmetrically relative to one of the other inner electrodes.

20 Claims, 4 Drawing Sheets

(51) Int. Cl.
*A61N 1/32* (2006.01)
*A61N 1/06* (2006.01)
A61B 18/00 (2006.01)
A61B 18/14 (2006.01)

(52) U.S. Cl.
CPC ............... *A61N 1/328* (2013.01); *A61N 1/40* (2013.01); *A61B 18/14* (2013.01); *A61B 2018/0016* (2013.01); *A61B 2018/00452* (2013.01); *A61B 2018/00577* (2013.01); *A61B 2018/1405* (2013.01); *A61B 2018/1467* (2013.01)

(56) References Cited

U.S. PATENT DOCUMENTS

| | | |
|---|---|---|
| 2008/0183251 A1 | 7/2008 | Azar |
| 2009/0118790 A1 | 5/2009 | Herk |
| 2013/0226269 A1 | 8/2013 | Eckhouse |
| 2013/0289679 A1* | 10/2013 | Eckhouse .............. A61N 1/403 607/102 |

FOREIGN PATENT DOCUMENTS

| | | |
|---|---|---|
| WO | 0135823 A1 | 5/2001 |
| WO | 2012023129 A1 | 2/2012 |
| WO | 2012052986 A2 | 4/2012 |

* cited by examiner

RADIO FREQUENCY SKIN TREATMENT DEVICE

This application is the U.S. National Phase application under 35 U.S.C. § 371 of International Application No. PCT/EP2015/060938, filed on May 19, 2015, which claims the benefit of European Application No. 14171173.9 filed on Jun. 4, 2014. These applications are hereby incorporated by reference herein.

FIELD OF THE INVENTION

The invention relates a device for skin treatment, in particular for radio frequency (RF) treatment of human skin. The device is primarily suitable for skin tightening and/or skin rejuvenation, in particular for fractional RF skin treatment. The invention also relates to the use of such a skin treatment device for both therapeutic and non-therapeutic purposes.

BACKGROUND OF THE INVENTION

Radio frequency (RF) is conventionally used in both the professional and home-use aesthetic market for skin tightening. The ability to heat a large volume at dermal skin level has made the radio frequency technology the standard for skin tightening and for treating skin laxity. Compared to laser treatments, RF devices have a relatively lower cost price and can provide larger-volume and deeper tissue contraction. Additionally, RF energy dissipation does not rely on absorption of light by chromophores, so that tissue pigmentation or the vascular network does not interfere with the delivery of energy.

The basic principle of RF energy delivery at the skin surface and from there to tissue is that an alternating current is applied in a closed circuit with the skin. Tissue impedance directly affects the extent of the heating: RF propagates more easily through tissues with high conductivity (low electrical resistance), while tissues with high electrical resistance (high impedance, low conductance) are poor conductors of RF energy. RF energy takes the path of least resistance through skin tissue and is dissipated as thermal energy primarily due to molecular vibrations.

A growing application for RF beyond skin tightening is skin rejuvenation. In most RF skin rejuvenation devices, fractional thermal lesions in the skin are created simultaneously using small electrodes. Recently, different professional devices have been launched onto the aesthetic market to address skin rejuvenation with a radio frequency device. Skin rejuvenation is a combination of different consumer benefits such as: even skin tone, reduction of pigmentation spots, improved radiance and texture and reduction of fine lines. Here the energy is used primarily to damage the stratum corneum and the epidermis (including the dermal-epidermal junction) and possibly the top part of the dermis. Traditionally, skin rejuvenation treatments are done by ablative or non-ablative settings of a laser wavelength which is highly absorbed by water, whereby the ablative treatments vaporize the skin and create hollow pillars in the skin and non-ablative treatments heat the skin to 65-100° C. to initiate cell necrosis and collagen denaturation and contraction and eventually collagen remodeling.

RF fractional skin treatment devices that use electrode configurations having a plurality of electrodes to simultaneously create a plurality of fractional thermal lesions have the disadvantage of inconsistency in RF energy delivery by the individual electrodes, resulting in the generation of non-uniform fractional thermal lesions. Non-uniformity of the thermal lesions in RF fractional skin treatments is due to a number of factors including variation in local tissue properties, e.g. skin impedance inhomogeneity, non-uniformity in electrode-skin contact, and inherent impedance variation due to the electrode configuration.

US 2013/0226269 discloses an apparatus for personal aesthetic skin treatment by RF voltage. The apparatus includes an RF voltage supply and a disposable patch with an assembly of individual electrodes operative to contact segments of the skin and deliver to each contact RF voltage. In one embodiment a rectangular patch is used comprising arrays of active RF electrodes arranged between elongated return electrodes. An another embodiment a circular patch is used comprising annular arrays of active RF electrodes surrounded by annular return electrodes.

SUMMARY OF THE INVENTION

It is an object of the invention to provide a device for RF skin treatment, in particular RF fractional skin treatment, that results in improved uniformity of the lesions. For this purpose, according to a first aspect of the invention, a device for radio frequency (RF) based skin treatment is provided comprising a non-circular outer electrode arranged on an operational side of the device and having at least one axis of symmetry. The device comprises at least two inner electrodes arranged on the operational side of the device, each of the inner electrodes having an equally shaped and equally dimensioned skin contact surface having an equal orientation relative to the operational side. An RF generator is arranged to supply an RF voltage between each of the at least two inner electrodes and the outer electrode. The outer electrode surrounds the at least two inner electrodes, and each of the at least two inner electrodes has an equal minimum distance to the outer electrode.

In case the outer electrode has only one axis of symmetry, the at least two inner electrodes are arranged so as to be symmetrically spaced from said one axis of symmetry.

In case the outer electrode has more than one axis of symmetry, each inner electrode is at an equal distance from a common point of intersection of all axes of symmetry and is positioned, with respect to each of the respective axes of symmetry, either on said respective axis of symmetry or at a distance from said respective axis of symmetry and symmetrically relative to one of the other inner electrodes.

The proposed electrode configuration creates, simultaneously, uniform thermal lesions in the skin tissue close to the individual inner electrodes. The lesions are uniform because the inner electrodes each deliver RF energy with the same RF current density and with the same RF field profile as a result of the symmetrical geometry of the electrode configuration. Depending on the temperature generated close to the inner electrodes, non-ablative thermolysis or tissue ablation is achieved close to the inner electrodes, while at other positions within the electrode configuration the skin temperature remains below the pain threshold. The electrodes may operate in a bipolar mode wherein the inner electrodes act as active electrodes and the outer electrode acts as a return electrode.

It is noted that the inner electrodes each have a skin contact surface with an equal shape and equal dimensions, and with an equal orientation relative to the operational side of the device. With "equal orientation" is meant an equal angular orientation relative to the operational side of the device, in particular relative to an outer skin contact surface of the device on which the electrodes are provided. Preferably the skin contact surfaces of the inner electrodes are parallel to the outer skin contact surface of the device, but alternatively the skin contact surfaces of the inner electrodes may have an equal inclination relative to the outer skin contact surface of the device.

In an embodiment, the outer electrode has n axes of symmetry, and surrounds at most 2n inner electrodes, where n is a positive integer.

In an embodiment, the outer electrode surrounds n inner electrodes, where n is greater than 1. For example, if the outer electrode is rectangular in shape, it will have 2 axes of symmetry and the outer electrode will then surround 2 inner electrodes. These 2 inner electrodes may lie on the axes of symmetry.

In another embodiment, the outer electrode surrounds 2n inner electrodes. Note that in this embodiment n can be 1 as well. In case the outer electrode only has 1 axis of symmetry, it will surround 2 inner electrodes. If the outer electrode has 2 axes of symmetry it will surround 4 inner electrodes. In this embodiment, all the inner electrodes are spaced from the axes of symmetry.

In an embodiment, the at least two inner electrodes have annular or disc-shaped skin contact surfaces. The term annular is to be taken to mean: circular having a certain width, and the term disc-shaped is to be taken to mean: a filled circle. Such electrodes are easy to manufacture. Furthermore, such electrodes do not have a favoured direction, so the shape does not locally influence the direction of the current passing through the skin. In a further embodiment, the at least two inner electrodes have rectangular or oval skin contact surfaces. In this embodiment an outer diameter of the skin contact surfaces of the inner electrodes may be in a range between 100 and 2000 μm, preferably in a range between 200 and 500 μm.

A contour of the outer electrode may be rectangular, triangular or oval. Other shapes are possible. The outer electrode will have at least one axis of symmetry.

In an embodiment, a skin contact surface of the outer electrode is at least 10 times larger than a total of the skin contact surfaces of all the inner electrodes. Such relative dimensions of the skin contact surfaces of the electrodes gave favorable results, wherein close to the outer electrode there was a minimal increase in skin temperature and no skin damage.

In an embodiment, an RF voltage supplied by the RF generator across each of the at least two inner electrodes and the outer electrode has a value and duration such as to cause, in use, localized thermolysis in the skin in the vicinity of the at least two inner electrodes at a temperature higher than 65° C. In another embodiment, the RF voltage supplied by the RF generator across each of the at least two inner electrodes and the outer electrode has a value and duration such as to cause localized non-ablative thermolysis in the vicinity of the at least two inner electrodes at a temperature between 65° C. and 100° C. In these embodiments, suitable values and durations of the RF voltage to cause the intended localized thermolysis effect can be determined experimentally. Alternatively, a skin temperature sensor can be applied to measure the local skin temperature, and a feed back control system can be applied to control the RF voltage depending on the measured skin temperature. Such methods to determine and/or control the RF voltage are well-known to the skilled person and can be applied by the skilled person in a straight-forward manner.

In an embodiment, the device comprises a plurality of inner electrodes and a plurality of outer electrodes, each of the plurality of outer electrodes surrounding at least two of the plurality of inner electrodes. By arranging a plurality of inner electrodes and surrounding them by outer electrodes, a larger surface can be treated at one time as compared to when only one outer electrode is used. At least some of the plurality of outer electrodes may be electrically connected to each other. The at least some of the plurality of outer electrodes may border each other, so as to form a lattice structure.

According to a second aspect, the invention relates to the use of the device as described above in the treatment of skin.

Further preferred embodiments of the device and method according to the invention are given in the appended claims, disclosure of which is incorporated herein by reference.

BRIEF DESCRIPTION OF THE DRAWINGS

These and other aspects of the invention will be apparent from and elucidated further with reference to the embodiments described by way of example in the following description and with reference to the accompanying drawings, in which.

The figures are purely diagrammatic and not drawn to scale. In the Figures, elements which correspond to elements already described may have the same reference numerals.

DETAILED DESCRIPTION OF EMBODIMENTS

Figure 1:
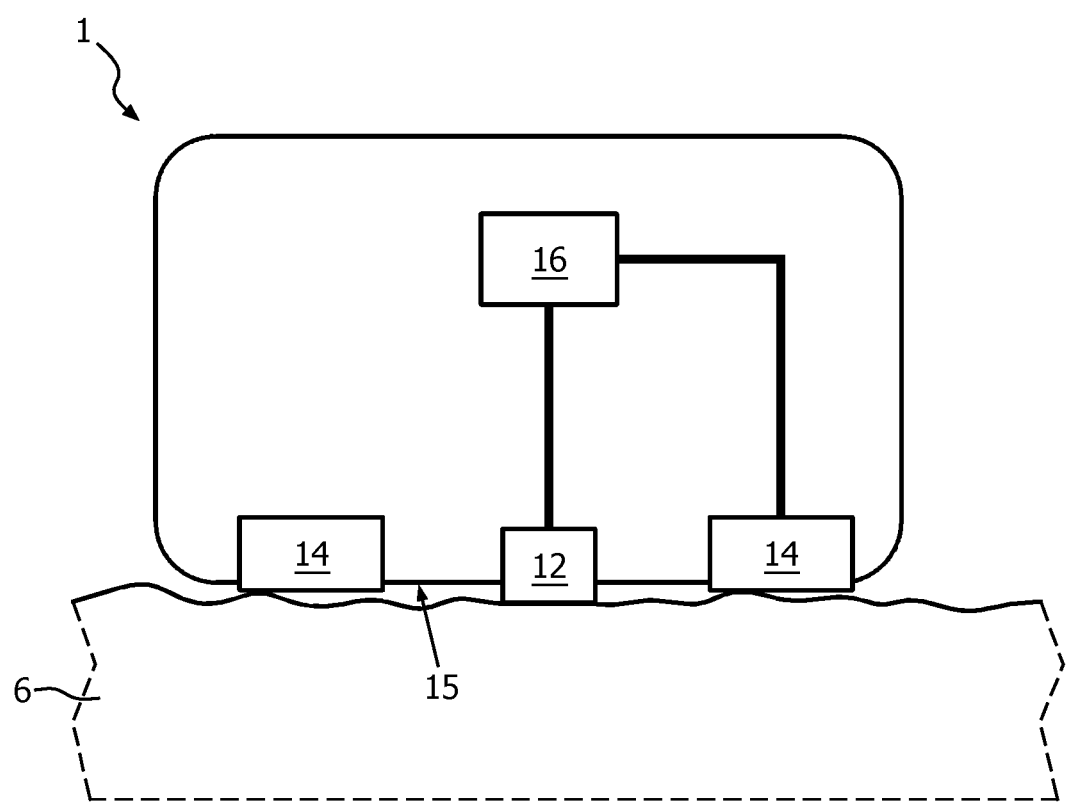
FIG. 1 is a schematic cross section of a device for skin treatment according to an embodiment.

FIG. 1 is a schematic cross section of a device 1 for skin treatment according to an embodiment. The device 1 comprises at least two inner electrodes 12 to be placed on the skin 6 of a user. It is noted that in this cross section only one inner electrode 12 is visible. The device 1 further comprises a surrounding (or outer) electrode 14 to be placed on the skin 6 of the user. The outer and inner electrodes are arranged on an operational side 15 of the device 1, forming an outer skin contact surface of the device 1. In use, the operational side 15 will face the skin of a user.

The outer electrode 14 is non-circular and is configured so as to surround the at least two inner electrodes 12. The outer electrode 14 has one or more axes of symmetry, as will be explained with reference to FIGS. 2A-2I. FIG. 1 also shows an RF generator 16 arranged to supply an RF voltage across each of the at least two inner electrodes 12 and the outer electrode 14. The RF generator 16 may be arranged to supply an RF voltage of 10-400V at a frequency of 0.2-300 MHz. In an embodiment, the RF voltage supplied by the RF generator across each of the inner electrodes and the outer electrode has a value and duration such as to cause, in use, localized thermolysis in the skin in the vicinity of the at least two inner electrodes at a temperature higher than 65° C. The value and duration of the RF voltage may be chosen so as to cause localized non-ablative thermolysis in the vicinity of the at least two inner electrodes at a temperature between 65° C. and 100° C.

The at least two inner electrodes 12 are surrounded by the non-circular outer electrode 14. Many different configurations are possible where the outer electrode 14 has at least one axis of symmetry. FIGS. 2A-2I show different possible configurations of the electrodes on the operational side 15 of the device 1.

Figure 2A:
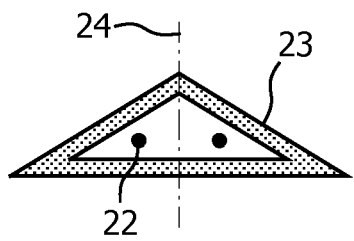
FIGS. 2A-2I show different embodiments of the electrodes.

FIG. 2A shows two inner electrodes 22 surrounded by a triangular outer electrode 23. The triangular outer electrode 23 has one axis of symmetry 24. The two inner electrodes 22 are at an equal minimum distance from the outer electrode 23. The minimum distance between an inner electrode 22 and the outer electrode 23 is determined by measuring the distance between points lying on an outer edge of the inner electrode 22 and points lying on an inner edge of the outer electrode 23. The minimum value of all these measured distances is the minimum distance mentioned.

Furthermore, the two inner electrodes 22 are symmetrically arranged relative to the axis of symmetry 24 and accordingly are at an equal distance from the one axis of symmetry 24. The distance between an inner electrode 22 and the axis of symmetry is defined as the minimum distance among all distances between points on an outer edge of the inner electrode 22 and the axis of symmetry 24.

Figure 2D:
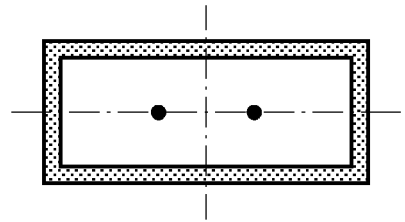
Figure 2B:
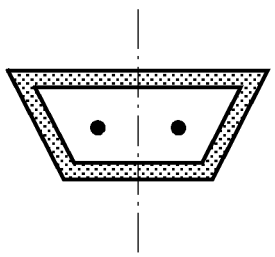
Figure 2E:
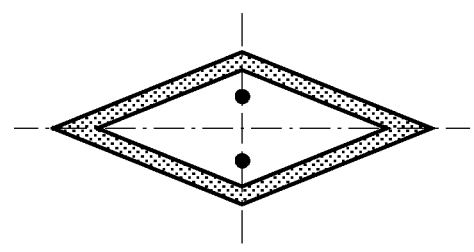
Figure 2C:
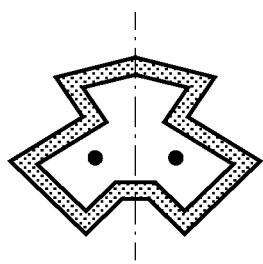

FIGS. 2B and 2C show examples of further possible electrode configurations with an outer electrode having one axis of symmetry, wherein two inner electrodes are arranged so as to be symmetrically spaced from the one axis of symmetry.

Figure 2F:
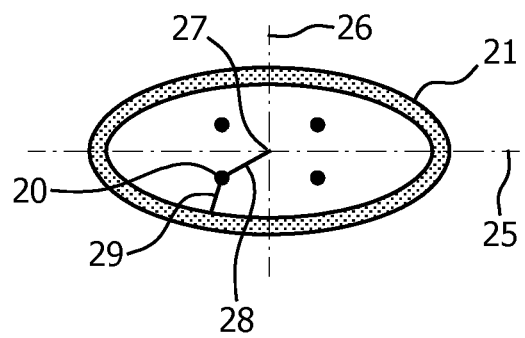

FIGS. 2D, 2E and 2F show examples of possible electrode configurations with an outer electrode having two axes of symmetry. In the case of two axes of symmetry, the number of inner electrodes can be two or four. FIG. 2F shows an example of an electrode configuration with four inner electrodes 20 surrounded by an oval outer electrode 21. The outer electrode 21 has two axes of symmetry 25 and 26. The four inner electrodes 20 are at an equal distance (see line 28) from an intersection 27 of the two axes of symmetry. Furthermore, the four inner electrodes 20 are at an equal minimum distance (see line 29) from the outer electrode 21. In the embodiments of FIG. 2D and FIG. 2E, the two inner electrodes are each positioned on one of the two axis of symmetry, and the two inner electrodes are symmetrically arranged relative to the other of the two axis of symmetry. In the embodiment of FIG. 2F, each of the four inner electrodes 20 is positioned, with respect to each of the two axes of symmetry 25, 26, at a distance from said axis of symmetry 25, 26 and symmetrically relative to one of the other inner electrodes 20.

Figure 2G:
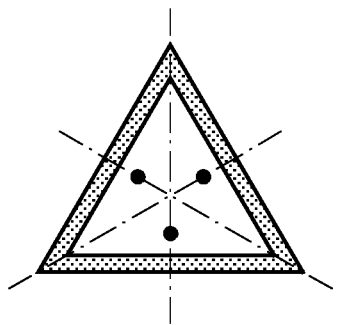
Figure 2H:
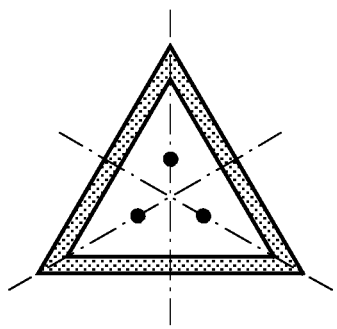
Figure 2I:
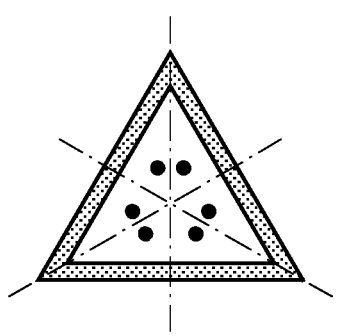

As can be seen from FIG. 2D, the outer electrode may be rectangular. Alternatively, the outer electrode may be triangular, as shown in FIG. 2A. Further possible electrode configurations with an equilateral triangular outer electrode are shown in FIGS. 2G, 2H and 2I. In each of these embodiments, the equilateral triangular outer electrode has three axes of symmetry. In the embodiments of FIG. 2G and FIG. 2H, three inner electrodes are provided which are each positioned on a respective one of the three axes of symmetry at an equal distance from the common point of intersection of the three axes of symmetry. In the embodiment of FIG. 2I, six inner electrodes are provided, wherein each inner electrode is at an equal distance from the common point of intersection of the three axes of symmetry, and wherein each inner electrode is positioned, with respect to each of the three respective axes of symmetry, at a distance from the respective axis of symmetry and symmetrically relative to one of the other inner electrodes.

According to an embodiment, the outer electrode has n axes of symmetry, and surrounds at most 2n inner electrodes, where n is a positive integer. So if, for example, the outer electrode is square-shaped, it will have 4 axes of symmetry and will surround at most 8 inner electrodes.

According to a particular embodiment, the outer electrode has n axes of symmetry, and the outer electrode surrounds n inner electrodes, where n is a positive integer greater than 1, such as 2, 3, 4, etc. So, if the number of axes is 2 then the number of inner electrodes is 2 as well. Examples of this embodiment are shown in FIGS. 2D and 2E. If the number of axes is 3, the number of inner electrodes is 3, see for example FIGS. 2G and 2H.

According to another embodiment, the outer electrode surrounds 2n inner electrodes, where n is a positive integer. If the number of axis is 1, the number of electrodes is 2, see for example FIGS. 2A, 2B and 2C. If the number of axes is 2, the number of inner electrodes is 4, see for example FIG. 2F. If the number of axes is 3, the number of inner electrodes is 6, see for example FIG. 2I.

The at least two inner electrodes have equally shaped and equally dimensioned skin contact surfaces, and the skin contact surfaces of the at least two inner electrodes have an equal orientation relative to the operational side 15, i.e. relative to the outer skin contact surface of the device. As a result, the contact impedance of the inner electrodes will be approximately equal for all inner electrodes, resulting in approximately equal electrical currents through the electrodes as a result of the symmetrical arrangement of the inner electrodes relative to the surrounding outer electrode as described in the embodiments here before. This will result in almost equal amounts of generated energy at the inner electrodes and thus more uniform lesions.

The inner electrodes 20, 22 may have annular or disc-shaped skin contact surfaces. Such shapes of the inner electrodes are relatively easy to manufacture. It is noted however that other shapes are possible, such as rectangular or oval.

Figure 3:
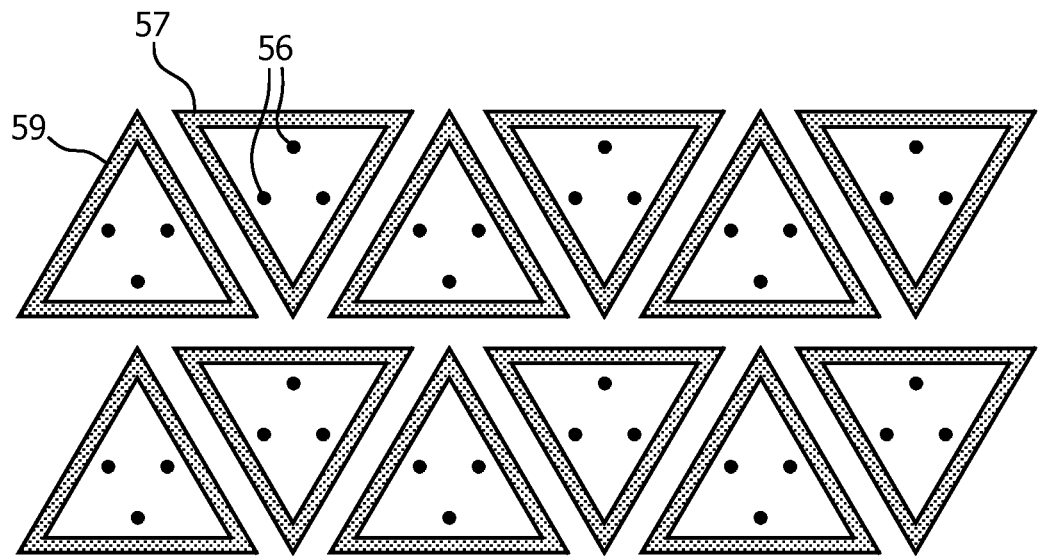
FIGS. 3 and 4 show embodiments wherein the device comprises a plurality of inner electrodes and plurality of outer electrodes.
Figure 4:
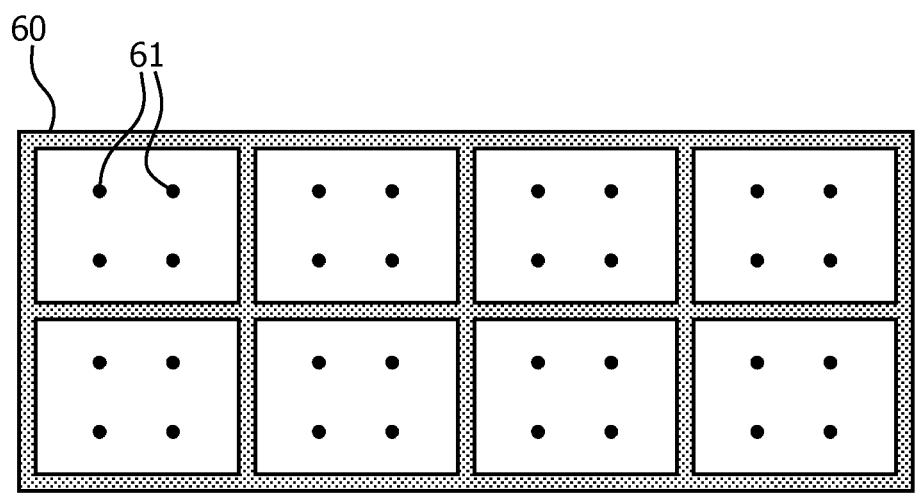

FIG. 3 shows an embodiment wherein the device comprises a plurality of inner electrodes 56 and a plurality of outer electrodes 57, 59. Each of the plurality of outer electrodes surrounds at least two of the plurality of inner electrodes. The configuration of each of the outer electrodes 57, 59 together with the associated inner electrodes 56 fulfills the constraints explained with reference to FIG. 2G, 2H or 2I. By arranging a plurality of inner electrodes and surrounding them by a plurality of outer electrodes, a larger surface can be treated at one time as compared to embodiments having only one outer electrode. In an embodiment, at least some of the plurality of outer electrodes are electrically connected to each other or partly border each other. This will require less wiring from the RF generator to the outer electrodes. Furthermore, more electrodes can be arranged on the same surface as compared to separate outer electrodes. FIG. 4 shows an embodiment wherein a plurality of inner electrodes 61 is surrounded by a plurality of square-shaped outer electrodes 60, wherein the outer electrodes 60 border each other. Each of the outer electrodes 60 surrounds four inner electrodes 61. As can be seen from FIG. 4, the outer electrodes 60 border each other so as to form a single lattice structure. In this case, only one electrical connection is needed for the outer electrode(s).

The invention also relates to the use of the device according to the embodiments described above in the treatment of skin. The device may be used for therapeutic or non-therapeutic (e.g. cosmetic) treatment. The device is especially useful for rejuvenation of the skin, but may just as well be used for skin tightening.

It is noted that in this document the word 'comprising' does not exclude the presence of elements or steps other than those listed and the word 'a' or 'an' preceding an element does not exclude the presence of a plurality of such elements, and it is also noted that any reference signs do not limit the scope of the claims. Further, the invention is not limited to the embodiments, and the invention lies in each and every novel feature or combination of features described above or recited in mutually different dependent claims.

The invention claimed is:

1. A device for radio frequency (RF) based treatment of a skin comprising:
   a non-circular outer electrode arranged on an operational side of the device and having at least one axis of symmetry;
   inner electrodes arranged on the operational side of the device, each of the inner electrodes having an equally shaped and equally dimensioned skin contact surface having an equal orientation relative to the operational side; and
   an RF generator arranged to supply an RF voltage between each of the inner electrodes and the outer electrode,
   wherein the outer electrode surrounds the inner electrodes, and wherein each inner electrode of all the inner electrodes is at an equal minimum distance from a respective nearest portion of the outer electrode, and wherein:
   in case the outer electrode has only one axis of symmetry, the each inner electrode of all the inner electrodes is arranged so as to be symmetrically spaced from said one axis of symmetry, and
   in case the outer electrode has more than one axis of symmetry and surrounds n of the inner electrodes where n is a positive integer other than 2 and 4, the each inner electrode of all the inner electrodes is at an equal distance from a common point of intersection of the more than one axis of symmetry and is positioned, with respect to each of the more than one axis of symmetry, either on the more than one axis of symmetry or at a same distance from the more than one axis of symmetry and symmetrically relative to one of the other inner electrodes.

2. The device according to claim 1, wherein the outer electrode has m axes of symmetry, the outer electrode surrounding at most 2m inner electrodes, where m is a positive integer and the at most 2m inner electrodes are other than 2 and 4 inner electrodes.

3. The device according to claim 2, wherein a respective one of the at most 2m inner electrodes is arranged on a respective one of the m axis of symmetry.

4. The device according to claim 1, wherein the outer electrode has m axes of symmetry and surrounds 2m inner electrodes, where m is a positive integer and the 2m inner electrodes are other than 2 and 4 inner electrodes.

5. The device according to claim 1, wherein the inner electrodes have annular skin contact surfaces.

6. The device according to claim 1, wherein the inner electrodes have rectangular or oval skin contact surfaces.

7. The device according to claim 1, wherein a contour of the outer electrode is rectangular, triangular or oval.

8. The device according to claim 1, wherein a skin contact surface of the outer electrode is at least 10 times larger than a total of the skin contact surfaces of all the inner electrodes.

9. The device according to claim 1, wherein the RF voltage supplied by the RF generator across the each inner electrode of all the inner electrodes and the outer electrode has a value and a duration such as to cause, in use, localized thermolysis in the skin in vicinity of the inner electrodes at a temperature higher than 65° C.

10. The device according to claim 1, wherein the RF voltage supplied by the RF generator across the each inner electrode of all the inner electrodes and the outer electrode has a value and a duration such as to cause localized non-ablative thermolysis in the skin in vicinity of the inner electrodes at a temperature between 65° C. and 100° C.

11. The device according to claim 1, wherein the device comprises a plurality of inner electrodes and a plurality of outer electrodes, each of the plurality of outer electrodes surrounding at least two of the plurality of inner electrodes.

12. The device according to claim 1, wherein the device comprises a plurality of inner electrodes and a plurality of outer electrodes, and wherein at least some of the plurality of outer electrodes are directly electrically connected to each other by sharing portions of adjacent outer electrodes.

13. The device according to claim 1, wherein the device comprises a plurality of inner electrodes other than 2 and 4 inner electrodes and a plurality of outer electrodes, and wherein the at least some of the plurality of outer electrodes share a border with each other, so as to form a lattice structure.

14. A device for radio frequency (RF) based treatment of a skin comprising:
   an outer electrode arranged on an operational side of the device;
   inner electrodes arranged on the operational side of the device; and
   an RF generator arranged to supply an RF voltage between each inner electrode of all the inner electrodes and the outer electrode,
   wherein the outer electrode surrounds the inner electrodes, and
   wherein the outer electrode has more than one axis of symmetry and surrounds n of the inner electrodes where n is a positive integer, and the each inner electrode is at an equal distance from a common point of intersection of the more than one axis of symmetry and is positioned, with respect to each of the more than one axis of symmetry, either on the more than one axis of symmetry or at a same distance from the more than one axis of symmetry and symmetrically relative to one of the other inner electrodes, and
   wherein the outer electrode has a shape which is one of a triangular, a parallelogram and a trapezoidal.

15. The device of claim 14 wherein a pair of the inner electrodes are 120° apart.

16. The device of claim 14, wherein the each inner electrode of all the inner electrodes has an equally shaped and equally dimensioned skin contact surface having an equal orientation relative to the operational side.

17. The device of claim 14, wherein n is an odd positive integer.

18. A device for radio frequency (RF) based treatment of a skin comprising:
   an outer electrode arranged on an operational side of the device and having at least one axis of symmetry;
   inner electrodes arranged on the operational side of the device; and
   an RF generator arranged to supply an RF voltage between each of the inner electrodes and the outer electrode,
   wherein the outer electrode surrounds the inner electrodes,
   wherein when the outer electrode has only one axis of symmetry, the inner electrodes are arranged so as to be symmetrically spaced from said one axis of symmetry, and
   wherein when the outer electrode has more than one axis of symmetry and surrounds n of the inner electrodes where n is an odd positive integer, each inner electrode of the inner electrodes is at an equal distance from a common point of intersection of the more than one axis of symmetry and is positioned, with respect to each of the more than one axis of symmetry, either on the more than one axis of symmetry or at a same distance from the more than one axis of symmetry and symmetrically relative to one of the other inner electrodes.

19. The device of claim 18, wherein each inner electrode of all the inner electrodes is at an equal minimum distance from a respective nearest portion of the outer electrode.

20. The device of claim 18, wherein a pair of the inner electrodes are 120° apart.

\* \* \* \* \*